US00PP21920P2

(12) United States Plant Patent
Kolster

(10) Patent No.: US PP21,920 P2
(45) Date of Patent: May 17, 2011

(54) ***WEIGELA* PLANT NAMED 'WINGS OF FIRE'**

(50) Latin Name: *Weigela florida*
Varietal Denomination: Wings of Fire

(76) Inventor: Hendrik Kolster, Boskoop (NL)

( * ) Notice: Subject to any disclaimer, the term of this patent is extended or adjusted under 35 U.S.C. 154(b) by 0 days.

(21) Appl. No.: 12/658,078

(22) Filed: Feb. 2, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell
(74) *Attorney, Agent, or Firm* — Penny J. Aguirre

(57) ABSTRACT

A new cultivar of *Weigela florida*, 'Wings of Fire', characterized by its bronze colored foliage from early summer to fall, its compact plant habit of medium stature, its large broad leaves, its red stems, and its resistance to wind and rain damage.

2 Drawing Sheets

Botanical classification: *Weigela florida.*
Variety denomination: 'Wings of Fire'.

BACKGROUND OF THE INVENTION

The present invention relates to a new and distinct cultivar of *Weigela florida* and will be referred to hereafter by its cultivar name, 'Wings of Fire'. 'Wings of Fire' is a new cultivar of old fashion *weigela*, a shrub grown for use as an ornamental landscape plant.

The new variety of *Weigela*, 'Wings of Fire', was selected from seedlings derived from open pollination in 2000 of an unnamed proprietary seedling of *Weigela florida* in the Inventor's garden in Booskoop, The Netherlands. 'Wings of Fire' was selected as a single unique plant from the resulting seedlings in summer of 2004.

Asexual reproduction of the new cultivar was first accomplished by the Inventor using softwood stem cuttings in 2004 in Boskoop, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for five years in Boskoop, The Netherlands. These attributes in combination distinguish 'Wings of Fire' as a unique cultivar of *Weigela.*

1. 'Wings of Fire' exhibits a compact plant habit of medium stature; reaching about 75 cm in height.
2. 'Wings of Fire' exhibits large, broad leaves.
3. 'Wings of Fire' exhibits bronze colored foliage from early summer to fall with color intensified with sun exposure.
4. 'Wings of Fire' exhibits red colored stems.
5. 'Wings of Fire' exhibits good resistance to wind and rain damage.

The female parent, a proprietary seedling, differs from 'Wings of Fire' in having bronze foliage only in fall and in having a second year habit that is less compact. 'Wings of Fire' can be most closely compared to the cultivars 'Alexandra' (U.S. Plant Pat. No. 10,772) and 'Elvera' (U.S. Plant Pat. No. 12,217). 'Alexandra' differs from 'Wings of Fire' in being taller in height (reaching about 1.5 m in height), in having a less compact plant habit and in having foliage that is darker bronze in color with distinct green veins. 'Elvera' differs from 'Wings of Fire' in having a dwarf plant habit (reaching about 22 cm in height) and in having foliage that is dark purple in color.

BRIEF DESCRIPTION OF THE DRAWING

The accompanying colored photographs illustrate the overall appearance and distinct characteristics of a 1 year-old plant the new *Weigela* as grown in a 1.5-liter container in Boskoop, The Netherlands.

The photograph in FIG. 1 provides an overall view of the growth habit of 'Wings of Fire'.

Figure 1:
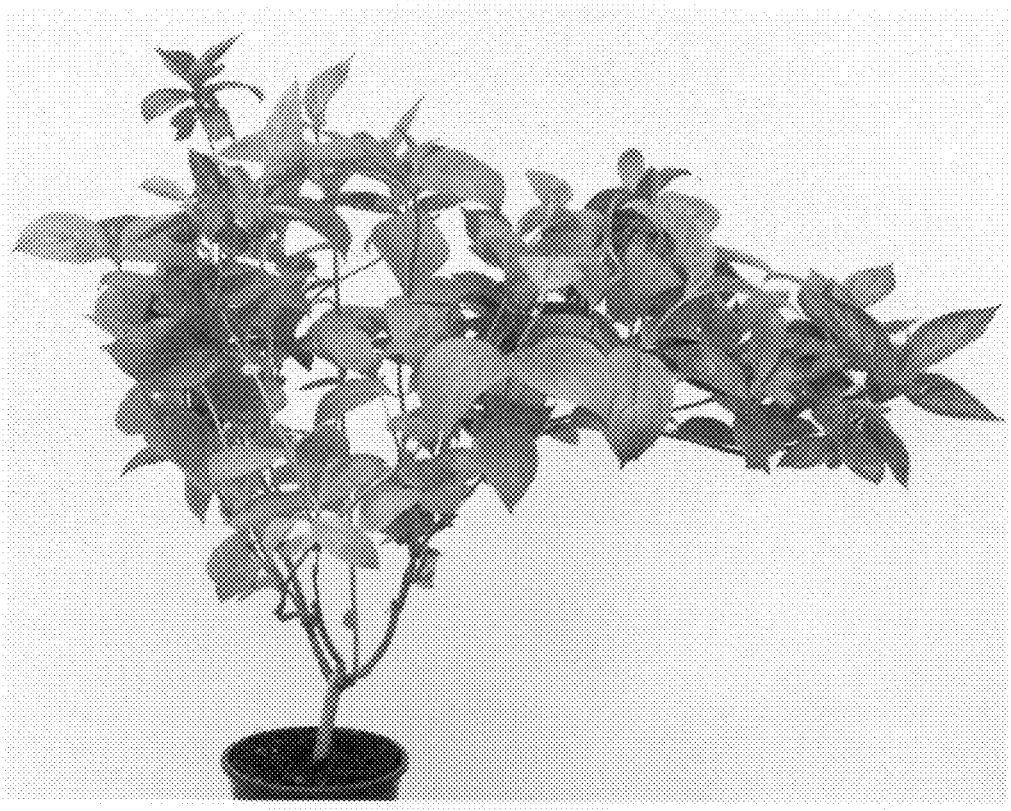
Figure 2:
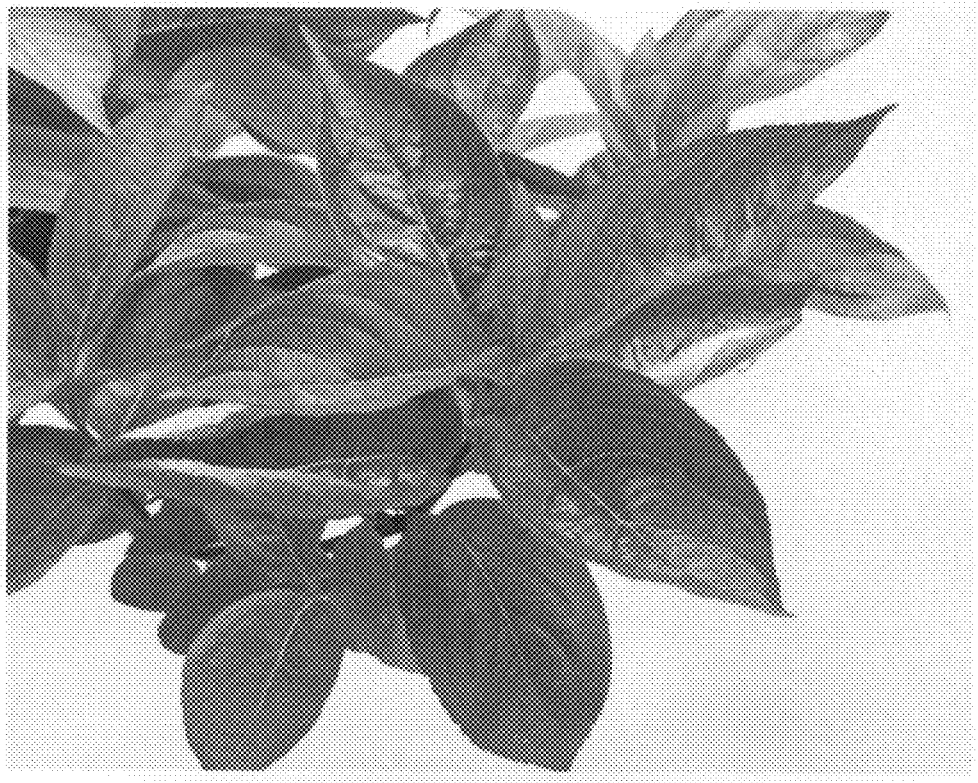

The photograph in FIG. 2 provides a close-up view of the foliage of 'Wings of Fire'.

Figure 3:
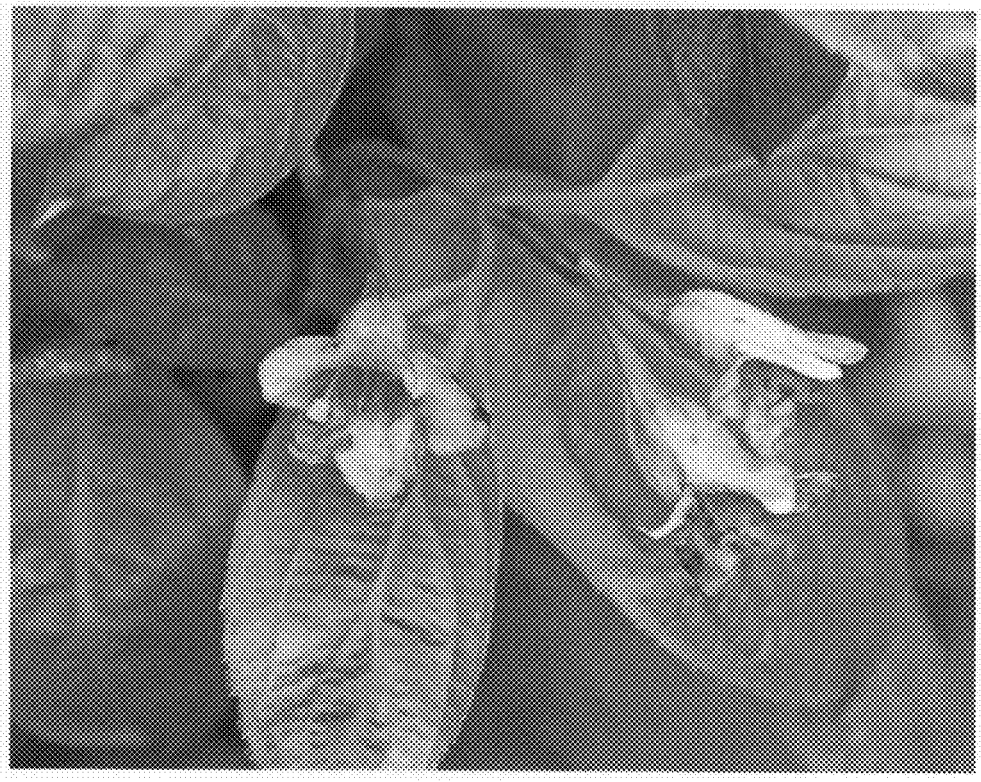

The photograph in FIG. 3 provides a close-up view of the flowers of 'Wings of Fire'. The colors in the photograph may differ slightly from the color values cited in the detailed botanical description, which accurately describe the colors of the new *Weigela.*

DETAILED BOTANICAL DESCRIPTION

The following is a detailed description of 1 year-old plants the new *Weigela* as grown in a 1.5 liter containers in Boskoop, The Netherlands. Plants were grown under average day temperatures of 15° C. to 28° C. and average night temperature of 4° C. to 18° C. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms for about 3 weeks in May in Boskoop, The Netherlands.

*Plant type.*—Deciduous shrub.

*Plant habit.*—Compact, broadly upright, freely branched, medium stature.

*Plant size.*—Reaches about 56 cm in height (75 cm in two years) and 56 cm in width in one year.

*Hardiness.*—At least in U.S.D.A. Zones 5 to 9.

*Environmental stress.*—Highly tolerant to wind and rain.

*Diseases and pests.*—No susceptibility or resistance to diseases or pests has been observed, similar to other *Weigela* cultivars known to the Inventor.

*Root description.*—Coarsely fibrous, moderately dense.

Growth and propagation:

*Propagation.*—Softwood stem cuttings.

*Root initiation.*—An average of 30 days at soil temperatures of 20° C.

*Root development.*—An average of 26 weeks at air temperatures of 18° C. to finish a young plant.

*Growth rate.*—Moderate to high, about 12 cm per month in spring.

Stem description:

*Shape.*—Quadrangular with older branches rounded.

*Stem color.*—New growth; 181B, mature wood; a blend of 199B and 199C.

*Stem size.*—Lateral branches; an average of 17.1 cm in length and 2.5 mm in diameter.

*Stem surface.*—New growth; moderately glossy with more terminal portion of stems pubescent with hairs about 1 mm in length and 155B in color, mature wood is dull and glabrous.

*Stem aspect.*—Upright to outward at an average angle of 15° from upright.

*Branching.*—Freely branched, an average of 30 lateral branches, pinching will increase branching but not required for a compact habit.

Foliage description:

*Leaf shape.*—Elliptic.

*Leaf aspect.*—Mature leaves strongly concave.

*Leaf division.*—Simple.

*Leaf base.*—Short attenuate.

*Leaf apex.*—Acuminate.

*Leaf fragrance.*—None.

*Leaf venation.*—Pinnate, upper surface 174C to 174D in color (145A to 145B on shaded leaves), lower surface 177D in color (144B on shaded leaves).

*Leaf margins.*—Finely serrate, pubescent with hairs about 0.5 mm in length and 157D in color.

*Leaf arrangement.*—Opposite.

*Leaf attachment.*—Petiolate.

*Leaf surface.*—Upper surface; moderately glossy with main vein moderately covered with hairs about 0.5 mm in length and 155A in color, lower surface; moderately glossy with main vein and secondary veins moderately covered with hairs about 0.5 mm in length and 157D in color.

*Leaf internode length.*—An average of 4.6 cm.

*Leaf size.*—An average of 9.2 cm in length and 5 cm in width.

*Leaf quantity.*—An average of 8 per stern.

*Leaf color.*—Newly expanded leaves; upper surface 143A to 143B and heavily tinged 177A to 177B, lower surface 138C to 148C tinged with 176A to 176B, mature leaves; upper surface 175A with shaded leaves 143B, lower surface 177D with shaded leaves 144B.

*Petioles.*—About 6 mm in length and 2 mm in width, color 147C, glabrous surface.

*Stipules.*—None.

Inflorescence description:

*Inflorescence type.*—Solitary or in pairs, at terminus and leaf axils.

*Inflorescence size.*—From about 2.6 cm in diameter and 4 cm in depth when a solitary flower and about 5 cm in diameter and 5 cm in depth when in pairs.

*Flower buds.*—Narrowly obovate in shape, an average of 2.8 cm in depth and 6 mm in diameter, 64A to 64B in color.

*Flower fragrance.*—None.

*Lastingness of flowers.*—About 12 days with about 90% of flowers in bloom at one stage, self-cleaning.

*Flower aspect.*—Outward to upright.

*Flower quantity.*—An average of 3 per stem, an average of 90 per plant.

*Flower type.*—Tubular.

*Flower size.*—Average of 2.6 cm in diameter and 4 cm in depth.

*Peduncles.*—Average of 1.5 cm in length and 1.5 mm in diameter, 176A in color, glabrous surface, oval in shape.

*Pedicels.*—None, sessile to peduncle.

*Calyx.*—Rotate in shape, an average of 1 cm in depth and 3 mm in width.

*Sepals.*—5, linear in shape, narrowly acute apex, narrowly cuneate base, entire margin, an average of 1 cm in length and 1 mm in width, 152C in color with margins 185B on upper surface and lower surface, surface is slightly glossy on both surfaces.

*Petals.*—5, lower 75% fused into tube, spathulate in shape, margin entire on free portion, apex obtuse, an average of 4 cm in length with free portion an average of 9 mm in width, outer and inner surface is smooth and slightly glossy, color of inner surface when opening and mature; N66D to 72D, color of outer surface when opening and mature; 70B, color fades to 63C and 63D on upper and lower surface.

Reproductive organs:

*Gynoecium.*—1 pistil, about 3.7 cm in length, style is an average of 3.5 cm in length, and N155C tinged with 62D in color, stigma is club-shaped and 155A in color, ovary is 176A in color.

*Androcoecium.*—5 stamens, filaments are 63D in color and an average of 1.1 cm in length, anthers are 159A in color, an average of 5 mm in length, basifixed and narrowly oblong in shape, pollen is low in quantity and 158D in color.

*Fruit and seed.*—No fruit or seed production has been observed to date.

It is claimed:

1. A new and distinct cultivar of *Weigela* plant named 'Wings of Fire' as herein illustrated and described.

* * * * *